United States Patent

Fünfschilling et al.

Patent Number: 5,371,230
Date of Patent: Dec. 6, 1994

[54] PHENYLPYRIDINE DERIVATIVES AND LIQUID CRYSTALLINE MIXTURES CONTAINING SAME

[75] Inventors: Jürg Fünfschilling, Basel; Stephen Kelly, Möhlin; Alois Villiger, Basel, all of Switzerland

[73] Assignee: Hoffmann-La Roche Inc., Nutley, N.J.

[21] Appl. No.: 160,373

[22] Filed: Nov. 29, 1993

Related U.S. Application Data

[62] Division of Ser. No. 896,030, Jun. 9, 1992, abandoned.

[30] Foreign Application Priority Data

Jun. 14, 1991 [CH] Switzerland ............... 1772/91

[51] Int. Cl.$^5$ ............................................. C07D 213/30
[52] U.S. Cl. .................................... 546/342; 546/341
[58] Field of Search ................................. 546/342

[56] References Cited

U.S. PATENT DOCUMENTS 4,752,413  6/1988  Inoue et al. .................. 546/342
4,898,455  2/1990  Buchecker et al. ............ 546/342

FOREIGN PATENT DOCUMENTS 242716  4/1987  European Pat. Off. .
2215571  9/1987  Japan .
3275563  11/1988  Japan .

OTHER PUBLICATIONS

Chemical Abstracts, vol. 109, No. 109:14928q (1988).
Derwent Abstract No. 87-304332/43 for Japan 87/215571.
Presentation as a Poster at the 14th International Liquid Crystal Conference—Jun. 21–26, 1992. Alkanoic acid 4-(5-alkyl-2-pyridinyl)phenyl esters: some novel smectic materials for display devices—S. M. Kelly, J. Funfschilling and A. Villiger.

*Primary Examiner*—C. Warren Ivy
*Assistant Examiner*—A. A. Owens
*Attorney, Agent, or Firm*—George M. Gould; George W. Johnston; Robert A. Silverman

[57] ABSTRACT

Compounds of the formula

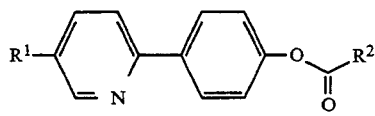

wherein $R^1$ signifies a straight-chain alkyl group with 7 to 9 carbon atoms; and $R^2$ represents a straight-chain alkyl group with 6 to 11 carbon atoms.

their manufacture, liquid crystalline mixtures which contain these compounds and their use for electro-optical purposes.

6 Claims, No Drawings

PHENYLPYRIDINE DERIVATIVES AND LIQUID CRYSTALLINE MIXTURES CONTAINING SAME this is a division of application Ser. No. 07/896,030, filed Jun. 9, 1992.

FIELD OF THE INVENTION

The present invention is concerned with phenylpyridine derivatives, liquid crystalline mixtures which contain these compounds and their use for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), SSF cells (surface stabilized ferroelectric), DHF cells (deformed helix ferroelectric) or SBF cells (short-pitch bistable ferroelectric).

The liquid crystal materials must have good chemical and thermal stability and good stability towards electric fields and electromagnetic radiation. Further, the liquid crystal materials should have low viscosity and in the cells should give short response times and high contrast. Furthermore, at usual operating temperatures of about −30° C. to about +80° C., especially of about −20° C. to about +60° C., they should have a suitable mesophase, for example, a broad smectic mesophase for the cells referred to above.

Since liquid crystals are usually used as mixtures of several components, it is important that the components have a good miscibility with one another.

SUMMARY OF THE INVENTION

The invention relates to compounds of the formula

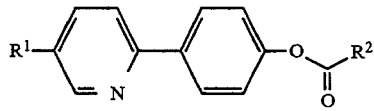

I wherein $R^1$ is a straight-chain alkyl group of 7 to 9 carbon atoms, and $R^2$ is a straight-chain alkyl group of 6 to 11 carbon atoms.

In addition, the invention relates to liquid crystalline mixtures having at least one compound of formula I.

DETAILED DESCRIPTION OF THE INVENTION

The present invention provides compounds of the formula

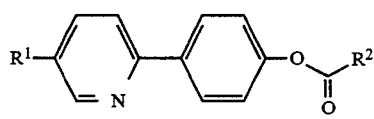

I wherein $R^1$ is a straight-chain alkyl group with 7 to 9 carbon atoms; and $R^2$ is a straight-chain alkyl group with 6 to 11 carbon atoms.

It has surprisingly been found that the compounds in accordance with the invention have extraordinarily favorable properties for ferroelectric applications. Although the compounds in accordance with the invention themselves frequently have no SC phase (smectic C phase), their admixture with known basic components for ferroelectric mixtures achieves a significant increase of the $S_C$—$S_A$ or $S_C$—N phase transition, a narrowing or even a complete suppression, of the $S_A$ phase. Moreover, the melting point is significantly lowered, which leads to a comparatively broad mesophase. Furthermore, the compounds in accordance with the invention have broad smectic phases with astonishingly low viscosity, which leads to rapid switching times.

The term "straight-chain alkyl group with 7 to 9 carbon atoms" means the groups heptyl, octyl and nonyl. The term "straight-chain alkyl group with 6 to 11 carbon atoms" means the groups hexyl, heptyl, octyl, nonyl, decyl and undecyl.

Compounds of formula I in which $R^1$ is octyl are preferred. Moreover, those compounds of formula I in which $R^2$ signifies heptyl, octyl or nonyl are especially preferred. These are examples of the preferred compounds:

4-(5-Octyl-2-pyridyl)phenyl octanoate
4-(5-Octyl-2-pyridyl)phenyl nonanoate
4-(5-Octyl-2-pyridyl)phenyl decanoate These compounds are characterized by an especially broad smectic mesophase range.

The compounds of formula I can be prepared in a manner known per se from a 4-(5-alkyl-2-pyridyl)-phenol and a fatty acid. The reaction can be effected in the presence of N,N'-dicyclohexyl-carbodiimide and 4-(dimethylamino)pyridine in, e.g., dichloromethane or another suitable solvent such as, e.g., chloroform. The compounds which are used as the starting materials are known and to some extent are commercially available.

The compounds of formula I can be used in the form of mixtures with one another and/or with other liquid crystal components. The compounds of formula I are preferably used in mixtures with other liquid crystal components.

The liquid crystalline mixtures in accordance with the invention contain at least 2 components, of which at least one component is a compound of formula I. A second component and, optionally, additional components can be further compounds of formula I, although at least one chiral dopant must be present in the mixture. Such further liquid crystal components are preferably a chiral compounds of the formulae

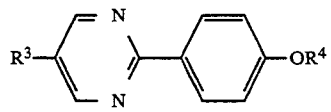

II

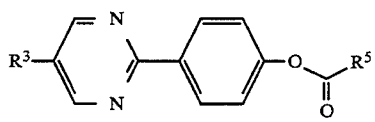

III

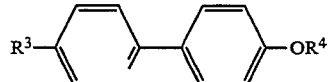

IV

Compounds of the following formulas are suitable as dopants:

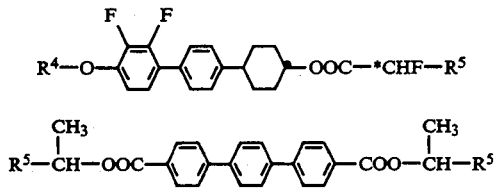

$$R^5-\overset{CH_3}{\underset{|}{CH}}-OOC-\text{⟨○⟩}-\text{⟨○⟩}-\text{⟨○⟩}-COO-\overset{CH_3}{\underset{|}{CH}}-R^5 \quad VI$$

wherein R³ denotes alkyl, alkoxy, 3E-alkenyl or 4-alkenyl; R⁴ signifies alkyl or alkenyl; and R⁵ signifies alkyl.

The term "alkyl" embraces unbranched or branched alkyl groups with 1 to 15 carbon atoms, preferably unbranched alkyl groups with 1 to 12 carbon atoms such as methyl, ethyl, propyl, butyl, pentyl, hexyl, heptyl, octyl, nonyl, decyl, undecyl and dodecyl.

The term "alkoxy" embraces ether groups in which the alkyl residue is as defined above.

The term "alkenyl" embraces alkenyl groups with 2 to 15 carbon atoms such as 2E-alkenyl, 3Z-alkenyl, 4-alkenyl and alkenyls having a terminal double bond.

The terms "2E-alkenyl", "3E-alkenyl", "3Z-alkenyl" and "4-alkenyl" embrace unbranched alkenyl groups with 3 to 15, 4 to 15 and, respectively, 5 to 15 carbon atoms in which the double bond is present in the 2, 3 or, respectively, 4-position, whereby E and Z denote the configuration of the double bond. Such groups are, for example, allyl, 2E-butenyl, 2E-pentenyl, 2E-hexenyl, 2E-heptenyl, 2E-octenyl, 2E-nonenyl, 2E-decenyl, 3-butenyl, 3E- or 3Z-pentenyl, 3E- or 3Z-hexenyl, 3E- or 3Z-heptenyl, 3E- or 3Z-octenyl, 3E- or 3Z-nonenyl, 3E- or 3Z-decenyl, 4-pentenyl, 4-hexenyl, 4-heptenyl, 4-octenyl, 4-nonenyl, 4-decenyl and the like. The term "alkenyl with a terminal double bond" embraces unbranched alkenyls with 3 to 15 carbon atoms such as, for example, allyl, 3-butenyl, 4-pentenyl, 5-hexenyl, 6-heptenyl, 7-octenyl, 8-nonenyl, 9-decenyl and the like.

With regard to the good solubility of the compounds of formula I and having regard to their good miscibility with one another, the content of compounds of formula I in the mixtures in accordance with the invention can be relatively high and can be up to 85 wt. %. A content of compounds of formula I of about 1–50 wt. %, especially of about 5–35 wt. %, is generally preferred.

The manufacture of the liquid crystalline mixtures and of the electro-optical devices can be effected in a manner known per se.

The invention is illustrated in more detail by the following Examples. In the Examples, C signifies a crystalline phase, N signifies a nematic phase, S signifies a smectic phase and I signifies the isotropic phase. The phase transition temperatures are given in each case as N-I (in this case transition from the nematic phase into the isotropic state).

EXAMPLE 1

4-(5-Octyl-2-pyridyl)phenol (0.5 g), 0.2 g of heptanoic acid and 0.04 g 4-(dimethylamino)pyridine were dissolved in 50 ml of dichloromethane and the solution was treated portion wise with 0.4 g of N,N'-dicyclohexylcarbodiimide within 10 minutes while stirring. The mixture was stirred at room temperature overnight and then filtered. The filtrate was diluted with dichloromethane, washed twice with 50 ml of saturated sodium carbonate solution each time and then with water, dried over magnesium sulphate, filtered and subsequently concentrated. The crude product obtained was purified by chromatography on silica gel with toluene. Recrystallization from ethanol gave 0.4 g of 4-(5-octyl-2-pyridyl)phenyl heptanoate with a m.p. (C—S) 57° C. and cl.p. (S—I) 77° C.

The following compounds were manufactured in an analogous manner:

4-(5-Heptyl-2-pyridyl)phenyl heptanoate, m.p. (C—$S_4$) 48° C., ($S_4$—$S_F$) 68° C., cl.p. ($S_F$—I) 74° C.;

4-(5-heptyl-2-pyridyl)phenyl octanoate, m.p. (C—$S_4$) 50° C., ($S_4S_F$) 68° C., ($S_F$—$S_C$) 76° C., cl.p. ($S_C$—I) 77° C.;

4-(5-heptyl-2-pyridyl)phenyl nonanoate, m.p. (S—$S_4$) 52° C., ($S_4$—$S_F$) 68° C., ($S_F$—$S_C$) 77.5° C., cl.p. ($S_C$—I) 78.5° C.;

4-(5-heptyl-2-pyridyl)phenyl decanoate m.p. (S—$S_4$) 56° C., ($S_4S_F$) 69° C., ($S_F$—$S_C$) 78.5° C., cl.p. ($S_C$—I) 81° C.;

4-(5-heptyl-2-pyridyl)phenyl undecanoate m.p. (C—$S_4$) 52° C., ($S_4$—$S_F$) 66° C., ($S_F$—$S_C$) 79° C., cl.p. ($S_C$—I) 81° C.;

4-(5-heptyl-2-pyridyl)phenyl dodecanoate, m.p. (C—$S_4$) 54° C., ($S_4$—SF) 68° C., ($S_F$—$S_C$) 79° C., cl.p. ($S_C$—I) 82° C.;

4-(5-octyl-2-pyridyl)phenyl octanoate, m.p. (C—S) 60° C. and cl.p. (S—I) 80° C., 4-(5-octyl-2-pyridyl)phenyl nonanoate, m.p. (C—S) 61° C. and cl.p. (S—I) 81° C., 4-(5-octyl-2-pyridyl)phenyl decanoate, m.p. (C—S) 61° C. and cl.p. (S—I) 83° C., 4-(5-octyl-2-pyridyl)phenyl undecanoate, m.p. (C—S) 42° C. and cl.p. (S—I) 83° C., 4-(5-octyl-2-pyridyl)phenyl dodecanoate, m.p. (C—S) 51° C. and cl.p. (S—I) 83° C., 4-(5-nonyl-2-pyridyl)phenyl heptanoate, m.p. (C—$S_C$) 60° C., cl.p. ($S_C$—I) 83° C.;

4-(5-nonyl-2-pyridyl)phenyl octanoate, m.p. (C—$S_C$) 66° C., cl.p. ($S_C$—I) 86° C.;

4-(5-nonyl-2-pyridyl)phenyl nonanoate, m.p. (C—$S_C$) 70° C., cl.p. ($S_C$—I) 87° C.;

4-(5-nonyl-2-pyridyl)phenyl decanoate, m.p. (C—$S_C$) 71° C., cl.p. ($S_C$—I) 89° C.;

4-(5-nonyl-2-pyridyl)phenyl undecanoate, m.p. (C—$S_C$) 66° C., cl.p. ($S_C$—I) 89° C.;

4-(5-nonyl-2-pyridyl)phenyl dodecanoate m.p. (C—$S_C$) 65° C., cl.p. ($S_C$—I) 90° C.

EXAMPLE 2

In order to investigate the properties of the compounds of formula I, a basic mixture was prepared and admixed in each case with 15% of a compound of formula I. The phase transition temperatures of these mixtures were determined; the crystallization temperature $T_c$ was determined from conductivity data. The switching times were measured at 25° C. (10 Vpp/μ, time from the start of the pulse to maximum current). The measured values are compiled in Tables 1 to 3.

Basic Mixture 16 wt. % of p-[trans-4-{[(R)-2-fluorohexanoyl]oxy}-cyclohexyl]phenyl 2,3-difluoro-4-(octyloxy)-benzoate;

24 wt. % of 2-[p-(hexyloxy)phenyl]-5-nonylpyrimidine;

24 wt. % of 2-[p-(nonyloxy)phenyl]-5-nonylpyrimidine;

12 wt. % of 2-[p-(nonyloxy)phenyl]-5-heptylpyrimidine;

12 wt. % of 2-[p-(heptyloxy)phenyl]-5-octylpyrimidine;

12 wt. % of 2-[p-(decyloxy)phenyl]-5-octylpyrimidine.

TABLE 1

| n | C/$S_X$-$S_C^*$ °C. | $S_C^*$-$S_A$ °C. | $S_A$-N °C. | N-I °C. | Switching time μsec |
|---|---|---|---|---|---|
| 6 | −7.8 | 59.6 | 63.7 | 70.1 | 95 |
| 7 | −6.9 | 61.1 | 64.9 | 70.3 | 95 |
| 8 |  | 61.0 | 63.7 | 66.1 | 105 |
| 9 | −10 | 62.5 | 66.3 | 70.5 | 105 |
| 10 | −8.1 | 62.5 | 66.0 | 70.2 | 110 |
| 11 | −8.4 | 61.5 | 65.5 | 69.9 | 105 |
| 12 | −7.8 | 62.7 | 67.2 | 71.4 | 110 |

EXAMPLE 3

The data for two mixtures for SBF applications, which contain representative compounds in accordance with the invention, are compiled in Table 2.

Basic Mixture 43 wt. % of bis[(S)-1-methylheptyl]-p-terphenyl 4,4'-dicarboxylate 28 wt. % of 2-[4-(hexyloxy)phenyl]-5-nonylpyrimidine;

29 wt. % of 2-[4-(nonyloxy)phenyl]-5-nonylpyrimidine;

Mixture I 16.5 wt. % of 4-(5-octyl-2-pyridyl)phenyl heptanoate
22.5 wt. % of 4-(5-octyl-2opyridyl)phenyl octanoate
61 wt. % of basic mixture Mixture II 21.5 wt. % of 4-(5-nonyl-2-pyrimidinyl)phenyl nonanoate
18 wt. % of 4-(5-nonyl-2-pyrimidinyl)phenyl decanoate
60.5 wt. % of basic mixture

TABLE 2

| Mixture | C/$S_X$-$S_C^*$ °C. | $S_C^*$-$S_A$ °C. | $S_A$-I °C. | $S_C$-I °C. | Switching time μsec |
|---|---|---|---|---|---|
| I | <−9 |  |  | 65.7 | 42 |
| II | >0 | 58.0 | 61.0 |  | 42 |

We claim:

1. A ferroelectric liquid crystalline mixture comprising at least two components, wherein at least one of the components is a compound of the formula

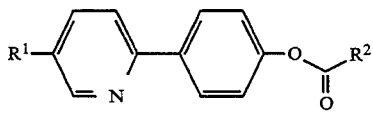

wherein $R^1$ is a straight-chain alkyl group with 7 to 9 carbon atoms and $R^2$ is straight-chain alkyl group with 6 to 11 carbon atoms,
and at least one of the other components is a chiral dopant.

2. The ferroelectric liquid crystalline mixture according to claim 1, wherein $R^2$ is heptyl, octyl or nonyl.

3. The ferroelectric liquid crystalline mixture according to claim 2, wherein $R^1$ is octyl.

4. The ferroelectric liquid crystalline mixture according to claim 3, wherein $R^2$ is heptyl.

5. The ferroelectric liquid crystalline mixture according to claim 3, wherein $R^2$ is octyl.

6. The ferroelectric liquid crystalline mixture according to claim 3, wherein $R^2$ is nonyl.

* * * * *